United States Patent
Benoit et al.

[11] Patent Number: 6,087,003
[45] Date of Patent: Jul. 11, 2000

[54] METHOD OF COATING PARTICLES AND COATED SPHERICAL PARTICLES

[75] Inventors: Jean-Pierre Benoit, Avrille; Hervé Rolland, Angers; Curt Thies, Ballwin; Vincent Vande Velde, Saint-Clement-de-la-Place, all of France

[73] Assignee: Centre de Microencapsulation, Angers, France

[21] Appl. No.: 08/817,305

[22] PCT Filed: Oct. 6, 1995

[86] PCT No.: PCT/EP95/03953

§ 371 Date: May 2, 1997

§ 102(e) Date: May 2, 1997

[87] PCT Pub. No.: WO96/11055

PCT Pub. Date: Apr. 18, 1996

[30] Foreign Application Priority Data

Oct. 6, 1994 [EP] European Pat. Off. ............. 94402251

[51] Int. Cl.$^7$ ....................................... B32B 5/16
[52] U.S. Cl. ................. 428/403; 118/50; 118/57; 118/624; 118/640; 118/724; 264/7; 264/9; 264/15; 264/574; 424/490; 424/497; 424/498; 428/407
[58] Field of Search ..................... 428/403, 407; 424/490, 497, 498; 427/212; 117/206; 264/7, 9, 15, 574; 118/724, 640, 50, 623, 624, 57

[56] References Cited

U.S. PATENT DOCUMENTS

| | | | |
|---|---|---|---|
| 3,874,907 | 4/1975 | Gardon et al. | 117/100 |
| 4,598,006 | 7/1986 | Sand | 424/81 |
| 5,043,280 | 8/1991 | Fischer et al. | 435/235.1 |
| 5,622,657 | 4/1997 | Takada et al. | 264/4.32 |
| 5,651,990 | 7/1997 | Takada et al. | 424/497 |
| 5,723,269 | 3/1998 | Akagi et al. | 424/497 |
| 5,753,261 | 5/1998 | Fernandez et al. | 424/450 |
| 5,766,637 | 6/1998 | Shine et al. | 424/497 |
| 5,770,459 | 6/1998 | Massey et al. | 436/526 |

FOREIGN PATENT DOCUMENTS

| | | |
|---|---|---|
| 0 616 801 A1 | 9/1994 | European Pat. Off. |
| 7205187 | 9/1973 | France. |

OTHER PUBLICATIONS

Journal of Aerosol Science; Pergamon Press; Particle Formation With Supercritical Fluids—A Review, Jean W. Tom and Pablo G. Debenedetti; Department of Chemical Engineering, Princeton University, Princeton, NJ 08544, U.S.A. (Received Oct. 24, 1990; and in final form Dec. 10, 1990).

Materials Science; Production of powders and films by the rapid expansion of supercritical solutions, Dean W. Matson, Robert C. Petersen, Richard D. Smith; Chemical Methods and Separations Group, Chemical Sciences Department, Battelle, Pacific Northwest Laboratories, Richland, Washington, USA (1987).

*Primary Examiner*—Hoa T. Le
*Attorney, Agent, or Firm*—Nixon & Vanderhye P.C.

[57] ABSTRACT

A microparticle comprising an active substance which is a central core made of liquid, gaseous or solid particle of regular or irregular shape, and the method for entrapping said active substance in a coating material which is conformationally distributed on said active substance and has a thickness ranging from the thickness of a monomolecular layer to about 100 $\mu$m. These compositions are useful for applications that require protection, prolonged release, taste masking, improved stability, altered handling behavior, altered surface properties including particle wettability, and other desirably altered properties.

17 Claims, 5 Drawing Sheets

METHOD OF COATING PARTICLES AND COATED SPHERICAL PARTICLES

FIELD OF THE INVENTION

This invention relates to the art of coating substances in the solid liquid or gaseous state, particularly solid particles and solid articles, especially solid articles with complex geometries or finite internal porous structures. In particular, this invention relates to a method for embedding or coating preformed particles or articles in solid liquid or gaseous state within a coating material to produce microparticles having an active substance entrapped in a layer of coating material. Such compositions are useful for applications that require protection, prolonged release, controlled release, taste masking, improved stability, altered handling behavior, altered surface properties including particle wettability, and other desirably altered properties.

BACKGROUND OF THE INVENTION

Many techniques for coating substances have been developed over the years. Nevertheless, there is a persistant need for new techniques able to coat a wide range of preformed solid particles. The reasons for this need are numerous. For instance, new applications for solid particulate materials and articles are developed consistently thereby requiring improved coating methods. Also, new coating materials are developed and require for their application new coating protocols. Furthermore, many existing coating protocols require the use of solvents which are often toxic or hazardous either to the environment, to personnel involved in a given particle coating protocol, or to the user of the particle. The latter situation arises when the final coated particle retains a finite amount of solvent(s) used in the coating of coated solid particles or articles. Further, solvents used in conventional solid particle or article coating processes may attack and partially dissolve the solid particles or articles being coated thereby altering properties of the solid particles or articles in some manner. Additionally, solvent-based coating formulations may cause mean size of particulate compositions being coated to increase measurably due to agglomeration caused by the nature of the solvent-based coating at the time of application.

A preponderance of current solid particle and article coating protocols involve deposition of liquid coating formulations on the surface(s) of the solid compositions being coated followed by solidification of said coating formulations. Solidification may occur because solvent is removed from the applied coating formulations, because the initially liquid coating formulations solidify due to cooling (e.g., they crystallize or pass below a glass transition temperature of the coating formulation during a cooling step), because initially liquid coating formulations are polymerized to a solid during the coating protocol, or because of a combination of these factors.

Supercritical fluids (SCF) in general, and supercritical carbon dioxide (SC $CO_2$) in particular, are prime vehicles by which improved coating technology can be developed and applied. They are protrayed as environmentally friendly fluids which can be used for a variety of economically useful purposes.

U.S. Pat. No. 4,598,006 discloses a method for impregnating a thermoplastic polymer with an impregnation material such as a fragrance or pest control agent or pharmaceutical composition wherein the impregnation material is dissolved in a volatile swelling agent for the thermoplastic polymer, said swelling agent being maintained at or near supercritical conditions.

U.S. Pat. No. 5,043,280 discloses a method and apparatus for the manufacture of a product having a substance embedded in a carrier that involves the use of a supercritical gas or supercritical fluid (SCF). The method consists of passing a liquid that contains a substance and carrier through a nozzle into a chamber loaded with a SCF thereby forming a gaseous mixture of the SCF and liquid medium, followed by separating the gaseous mixture of SCF and liquid medium to produce a sterilized product comprising a substance embedded in a carrier.

SUMMARY OF THE INVENTION

The invention relates to microparticles comprising an active substance, preferably an active substance in the form of a solid particle or an inert porous solid particle having absorbed therein an active substance in the liquid state or dissolved in a suitable solvent, the active substance or the inert solid being entrapped within a coating including a layer of a coating material. The microparticles are characterized in that the layer of coating material is conformationally distributed on the active substance and has a thickness ranging from the thickness of a mono-molecular layer to about 100 $\mu$m, preferably to about 40 $\mu$m. Preferably, the active substance found in the microparticles of the present invention is a central core comprising a liquid, gaseous or solid particle of regular or irregular shape. In the case of a solid particle of irregular shape, the coating of the microparticles of the present invention follows the surface of the particles being coated, including internal pores and crevices. The particle size of the microparticles of the present invention ranges in diameter from 1 nm to about 1 cm, preferably from 20 nm to 100 $\mu$m.

In another embodiment of the present invention, the coating of the microparticles of the present invention comprises a plurality of layers of identical or different coating materials. The thickness of each layer may be identical or different.

Also within the scope of the present invention is a composition comprising a plurality of microparticles of even or uneven size distribution. The microparticles comprise an active substance conformationally entrapped within a layer of a coating substance having a thickness ranging from the thickness of a monomolecular layer to about 100 $\mu$m. Preferably, the active substance of the microparticles forming the composition of the present invention is a central core comprising a solid particle.

The invention also relates to a process for entrapping an active substance, preferably a solid particle or an inert porous solid particle having the active substance absorbed therein, in a coating material. The process comprises suspending an active substance in a supercritical fluid containing a coating material dissolved therein under conditions which cause substantially no swelling and/or dissolution effect on the inert porous solide particle or the active substance if the active substance is in the solid state. The temperature and/or pressure of the supercritical fluid is then gradually reduced under controlled conditions to reduce the solubility of the coating material in the supercritical fluid to cause the coating material to be deposited onto the active substance. Particularly, the process is characterized in that the active substance is in the form of liquid droplets, gas, preferably in the form of solid particles or in the form of a liquid in which the solid substance is being dissolved, the liquid absorbed in a porous solid substrate. The liquid droplets, gas or preferably the solid particles are constantly agitated or stirred during their exposure to the supercritical fluid containing the coating material dissolved therein. More particularly, the active substance is a solid particle and the conditions under which the solid particle is coated by the coating material are chosen to maintain the physical integrity of the solid particle in other words to avoid solubilization of the solid particle throughout its contact with the SCF.

The process of the invention can also comprise further step in which the coating material deposited onto the active substrate is cured in a controlled manner.

In practising the process of the present invention, the active substance and the coating material can be placed in an autoclave which is then filled with a supercritical fluid under conditions of temperature and pressure required to dissolve the coating material in the supercritical fluid. Alternatively, the active substance can be placed in a autoclave which is then filled with a supercritical fluid containing the coating material already dissolved therein.

The present invention also relates to an apparatus for depositing a coating material dissolved in a supercritical fluid onto an active substance. The apparatus comprises a reservoir/reaction chamber capable of receiving and maintaining a gas under supercritical conditions, and a pressurizable reaction chamber in fluid communication with the reservoir/reaction chamber. The reaction chamber comprises stirring means to suspend the active substance when the supercritical fluid is introduced in the reaction chamber. The apparatus also comprises means for controlling the temperature and/or the pressure in the reaction chamber. Preferably, the stirring means is an agitator including a magnetic transmissions stirrer.

Particularly, the apparatus of the present invention can further comprise reservoir means in fluid communication with the supercritical gas condenser for dissolving the coating material in the supercritical fluid.

The final result is coated active substances in tire form of solids, liquids, gases, particles or articles with desireable properties obtained without the use of usual organic solvent (s). The coated active substances have a controlled thickness and/or geometry of coating material and are isolated after the coating system is depressurized to atmospheric pressure and returned to room temperature if the coating was done at some temperature other than room temperature.

Particularly, the invention relates to the coating of preformed solid particles or articles by controlled changes in a system that initially contains a mixture of a SCF and a coating material dissolved thereon. The mixture is maintained at temperature and pressure conditions under which the solid particles or articles are insoluble in the SCF. The temperature and/or pressure of the system is subsequently altered in such a manner as to cause controlled precipitation and/or crystallization of the coating material from the SCF phase onto the surface of the exposed solid particles or articles thereby forming coated solid particles or articles. The solid particles can be porous inert particles in which is absorbed an active substance dissolved in a solvent not miscible or having a substantially weak affinity for the SCF in which the coating substance is dissolved.

One of the important advantages of the process of the present invention resides in the fact that the resulting microparticles are substantially free of pores exposing the active material either in liquid, gaseous or solid form, to external conditions. The reason for this is that since the active substance is not dissolved in the SCF, upon return to normal pression conditions, the SCF does not escape from the central core to create important channels in the coating material and if the active substance is a solid particle. The SCF only escapes from the thin layer of coating material and temperature and pression conditions can be varied to promote a gradual escaping of the SCF from the coating material, thereby avoiding substantial pore formation. Also, because the process of the present invention does not require spraying of the active substance under which coating must be performed very quickly, and because the active substance is not solubilized in the SCF, it is possible to successively apply multiple layers of either identical or different coating materials onto the active substance. In order to do so, the temperature and pressure parameters of the SCF can be varied in a controlled manner to achieve desired dissolution and subsequent solidifying of the coating material. dr In the drawings:

DETAILED DESCRIPTION OF THE PREFERRED EMBODIMENTS

Figure 1:
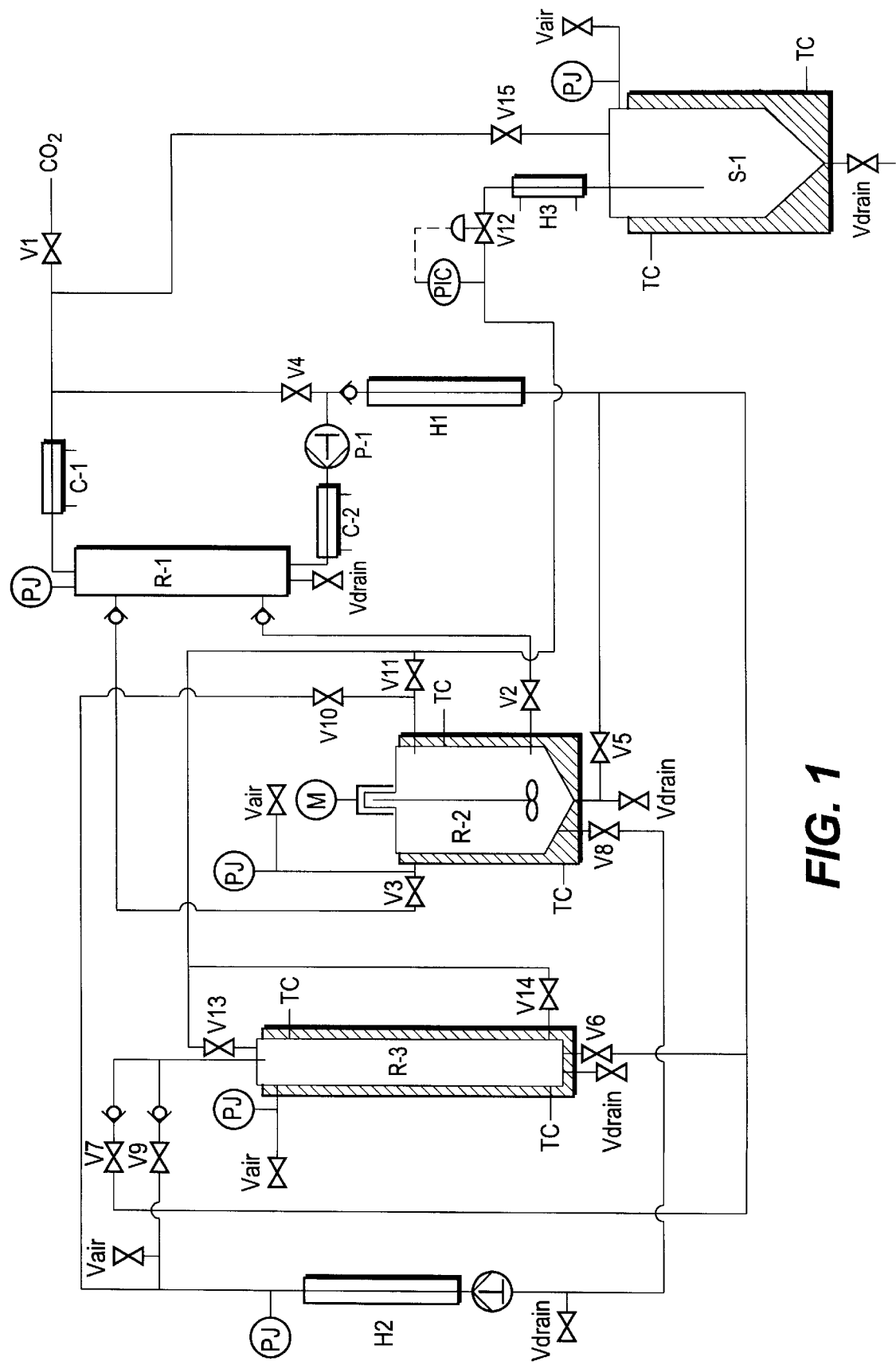
FIG. 1 illustrates a complete schematic representation of a preferred embodiment of the apparatus of the invention.

In accordance with the method of this invention, coating materials dissolved in a SCF are deposited in a controlled manner on the surface of active substances such as solutions of active substances, melted active substances, emulsions, solid particles or articles which are insoluble in or unaffected by SCF, thereby producing the desired coating.

Coating materials

Preferred coating materials are materials soluble in a SCF (e.g., supercritical $CO_2$) under conditions that do not substantially alter or affect the substrate being coated or the material(s) being used as coating material(s). Candidate coating materials include materials typically generically classified as lipids. Specific examples are mono- di- and tri-glycerides of various fatty acids like monostearin, distearin, tristearin, monopalmitin, dipalmitin, tripalmitin, monolaurin, dilaurin, trilaurin, as well as various combinations of these and related fatty acid glycerides. Glycerides produced by acetylation of mono- or di-glycerides, or by hydrogenation of various liquid glycerides to thereby produce solid fats (e.g., hydrogenated vegetable oils of all types) are also candidates. Other candidate lipids are fatty alcohols like stearyl alcohol and palmityl alcohol, fatty acids like stearic acid, palmitic acid, myristic acid, and lauric acid, and combinations of these materials with other lipids. Still other candidate generic lipids are assorted waxes like beeswax, caranauba wax, paraffin waxes, or combinations, of these and other waxes with each other or with the assorted glycerides mentioned previously. Still other candidate lipid coating materials are cholesterol, various cholesterol derivatives, and various combinations of these lipids with various combinations of the aforementioned lipids known as glycerides, fatty acids, fatty alcohols, and waxes. Still other candidate coating materials are lecithin, shellac, and natural or synthetic organic polymers of assorted types.

Some of the substances which can be used as coating substances in the context of the present invention can require the use of an entrainer substance for the solubilization into the SCF. An entrainer is a substance that when dissolved in small amounts in a SCF greatly increases solubility of the material(s) being dissolved in the SCF, in the present case, the coating material(s), without having substantial effect on the SCF properties of the primary component of the SCF system or density of the SCF system.

Specific nonlimiting examples of coating materials that often require the use of an entrainer include shellac, as well as natural or synthetic polymers such as assorted polyester and polyanhydride polymers commonly classified as biodegradable. Such polymers include all poly(lactide) homopolymers and copolymers with glycolic acid as well as polyglycolide homopolymer. Such polymers as well as their properties are described in detail in EP 052510, U.S. Pat. No. 3,887,699, EP 0548481 and U.S. Pat. No. 3 773 919. Poly($\epsilon$-caprolactone), poly($\beta$-hydroxybutyrate), poly (hydroxyvalerate) and $\beta$-hydroxybutyrate-hydroxyvalerate copolymers. Other candidate coating materials that may require the use of an entrainer include a variety of polymers formed by free radical polymerization or polycondensation representative examples of which include polystyrene, poly (methyl methacrylate), poly(vinyl chloride), polyvinyl alcohol, polyvinyl esters (like polyvinyl acetate or polyvinyl phtalate), and polyvinyl pyrolidone, poly(dimethyl siloxane), polysulfone, assorted polyamides (or nylons), poly(ethylene terephthlate), polyolefins like polypropylene, polyethylene and its copolymers with acrylic or methacrylic acid or acrylate esters like methyl methacrylate and butyl methacrylate, polysaccharides and their derivatives such as cellulose, chitosan, carraghenane and their derivatives.

Combinations of assorted coating materials can be applied either by sequential deposition of the different candidate coating materials under different SCF operating conditions or, if different combinations of coating materials are deposited simultaneously, said deposition of combinations of materials occurs from a given SCF system under conditions where, prior to the deposition step, said combination of coating materials has measurable solubility in the SCF system being used and during the coating material deposition step, said combination of materials has equal affinity for the surface being coated so that one material is not deposited to the total exclusion of the other material(s).

Supercritical fluids

In the case of supercritical $CO_2$ (SC $CO_2$), typical initial operating conditions will be approximately 31 to 80° C. and pressures of 70 to 250 bars, although higher values of either or both parameters can be used, provided, of course, that the higher values have no deleterious effect on the substrate being coated. With SCF systems other than SC $CO_2$, minimal operating temperatures and pressures will be those necessary to form a SCF with such systems. Ref. 2 specifies these conditions for a number of materials commonly used as SCF. Tom and Debenedetti (Ref. 1) say that normally the term supercritical is reserved for fluids that exist within the following approximate reduced temperature and reduced pressure range: $1.01 < T_r < 1.1$ and $1.01 < P_r < 1.5$, where $T_r$, the reduced temperature, is the ratio of the actual operating temperature (° K.) of the system to the critical temperature (° K.) of the material(s) that serves as the SCF while $P_r$, the reduced pressure, is the ratio of the actual operating pressure (can be specified in any established pressure units) of the system to the critical pressure (same pressure units used to specify the actual operating pressure) of the material(s) that serves as the SCF. In all cases, maximal operating temperatures and pressures for the purpose of this disclosure will be defined as those that begin to cause measurable undesireable alteration of properties of the substrate(s) being coated. These maximal operating conditions normally are conditions that cause melting of the substrate, in case preformed solid particles are used, chemical degradation of the substrate, or some other undesireable change in property of the substrate. The SCF used may or may not contain an entrainer. As noted above, an entrainer is defined as a substance deliberately added to a SCF system in small amounts in order to enhance solubility of a given substance (s) in said SCF system. When an entrainer is present in a small amount in the SCF (e.g., <5%), an amount so small that its presence has essentially no effect on the conditions needed to enter the supercritical state of the primary component of the SCF system, it greatly enhances solubility properties of the coating material(s) in the chosen primary SCF component. Candidate entrainers include but are not limited to ketones, alcohols, esters and chlorinated solvents, as Nell as other well recognized organic solvents and plasticizers. Entrainers are used in cases where the candidate coating material(s) has little solubility in the preferred SCF.

Substances to be coated

The active substances to be coated using the concept of the present invention can be either liquids, solids or gases but are preferably liquids and solids. The only requirement is that these substances be or have the possibility to be rendered insoluble in the SCF in conditions required to dissolve the coating material.

Examples of active substances which can be coated in accordance with the present invention include organic and inorganic compounds and peptides which find applications in pharmaceutical compositions, agrochemical compositions, human and animal food compositions, imaging compositions, ink compositions, cosmetic compositions, fragrance compositions, adhesive compositions and the like. Particularly, preferred are pharmaceutical compositions which may require a coating either to mask the taste or to enable sustained release of active substances embedded in biodegradable polymers such as those mentioned above. Preferred active substances include cimetidine, ranitidine, ibuprofen, acetaminophen, erythromycin, LHRH analogs such as buserelin, deslorelin, gonadorelin, goserilin, histrelin, leuprorelin, nafarelin or triptorelin, pamoate, tannate, stearate or palmitate of a naturally occurring or synthetic peptide comprising from 3 to 45 amino acids including LHRH, somatostatine, GH-RH or calcitonine . Other active substances include neurotrophic factor, ciliary neurotrophic factor, fibroblast growth factor, glial derived neurotrophic growth factor, brain derived neurotrophic factor nerve growth factor, vaccines, insuline, morphine and its derivatives and antibiotics.

In the event the substance to be coated is a solide particle, a wide variety of solid particles can be coated using the process of the invention.

Examples are powders formed by crystallization, precipitation, pyrolysis, or evaporation of solvent from a solution that initially contained a dissolved solute, powders formed by grinding, milling, crushing, or any other mechanical size reduction process, powders formed by polymerization of monomers to form polymeric particles, powders formed by granulation, prilling, and encapsulation techniques including spray drying, hot melt processing, and extrusion-coextrusion processing, naturally occurring powders such as clays and inorganic pigments, and powders formed by any other means. A significant feature of the process of the present invention is that it can be used to coat particles of a wide range of geometries including particles of very regular and irregular geometry. The process can be used to coat perfect spheres, highly regular but nonspherical crystals having a wide range of characteristic crystal habits (e.g., cubic, octahedronal, triclinic, etc.), and highly irregular particles typical of those formed by by conventional size reduction processes. Porous solid particles and articles are additional candidate substrates to be coated by the process disclosed herein because the process involves controlled deposition of a coating by "condensation", precipitation, or crystallization of the intended coating material on the surface of the solid particles and articles directly from the supercritical state so that there is no concern about a viscous coating solution formed with conventional solvents adequately penetrating the pores and crevices of the substance to be coated. Indeed, a feature of the coating technology disclosed in this application is the ability of this technology to deposit a conformational coating. That is, a coating that follows the surface of the particle(s) or article(s) being coated including internal pores and crevices. Further, coatings composed of different coating materials can be deposited in layers onto the external and internal surfaces of solid particles and articles desired to be coated, said coatings ranging in thickness from molecular dimensions up to macroscopic dimensions, preferably from the thickness of a mono-molecular layer to about 100 pm, preferably to about 40 $\mu$m.

In one of the applications of the present invention, a porous solid particle is used to allow coating of an active substance which for example cannot be made solid at the desired temperature. In these situations, the active substance is usually either in the liquid state or for instance dissolved in a solvent which has no affinity for the SCF. The active substance is abs orb ed in the porous solid particle. If the amount of liquid absorbed on the porous solid particle is such that the strutural integrity of the particle can be maintained for at least a limited period of time of about 30 minutes to 4 hours. The porous particle can be coated using the process of the present invention. The absence of affinity or miscibility of the liquid containing the active substance for the SCF further maintains this liquid in the porous substrate and avoids deep penetration of the SCF in the pores of the substrate. Once the porous substrate has been coated using the process of the invention, the active substance is trapped in the solid substrate and is released from it as the coating dissolves.

An additional feature of the coating process disclosed herein is that it can be used to deposit, as a coating on a solid substrate, a specific fraction of material from a candidate coating material that is in reality a complex mixture of different components and not a single component material. This type of precise deposition of coating material is something that is vertually impossible to do by other coating techniques. Many, if not most, candidate coating materials in commercial use are known to be complex mixtures of various substances. Nonlimiting examples include natural materials like fats and waxes, materials derived from natural materials like hydrogenated fats, and synthetic materials like paraffin waxes. Other materials often sold as essentially single component materials may contain up to 5–10% of assorted other components often classified as impurities, it being well known that production of absolutely pure materials for commercial use is generally a prohibitively costly task for commercial coating processes. The assorted substances present in many materials, such as those mentioned above, affect properties of the coated material in some manner. Accordingly, a SCF pre-extraction step under a specific set of operating conditions can be carried out in order to selectively remove assorted components of a candidate coating material deemed to be undesireable for a planned application thereby providing a precisely purified material that can be used as the coating material. Remarkably, this step can be conveniently carried out immediately before deposition of the coating material on a substrate is made to occur, so there is no question that the coating material is properly purified at the time it is deposited on a substrate. Another possibility is to use a specific set of SCF operating conditions to selectively extract very specific component(s) from a complex mixture and subsequently cause said component(s) to deposit on a substrate thereby producing a coating that is made up only of the specific selected component(s).

General outlines of the process of the invention

Deposition of a coating by the process disclosed herein involves altering the temperature and pressure of a SCF in which the desired coating material(s) is dissolved. This alteration is carried out in a controlled manner so that the desired coating material(s) either crystallizes on the surface of the substrate being coated or precipitates there. The process disclosed herein is not based on rapid precipitation, with or without subsequent crystallization, of materials initially dissolved in a SCF, to form free or self-standing small particles containing a combination of active substance or carrier material. This type of configuration, if it occurs, is the result of improper system operating conditions for deposition of the intended coating material(s). The process disclosed here is based on the controlled deposition of coating material(s) on the liquid droplets of an emulsion, on a volume of gaseous particles or on the external and internal surfaces of preformed solid particle(s) and article(s).

In the case of solid particles, the molecular interactions or attractions of dissolved solutes for solid surfaces are used to initially attract and guide the coating molecules, initially dissolved in the SCF system used to the surface being coated. This phenomenon in conventional liquid/solid and gas/solid systems is known as adsorption. The SCF containing the dissolved coating material(s) can be viewed as a solution, perhaps a nonconventional solution since the solute is dissolved in a SCF, but nevertheless a solution in which the coating material(s) is molecularly dissolved and hence, a solution from which solute adsorption can occur to thereby form a coating which can serve many useful functions and have many different compositions, thicknesses and properties. The coating material(s) dissolved in the SCF are solutes that can freely penetrate space that the SCF penetrates provided their molecular size allows them to pass into an internal pore or fissure or crack in a given solid particle or article and hence, can be deposited therein. There is no concern about problems of making a viscous coating solution penetrate internal pores, cracks, and fissures characteristic of many solids.

Hence, when a solid substance is to be coated according to the process of the invention, adsorption of a specific coating maternal is made to occur and/or slowly enhanced during the process disclosed herein by altering the temperature and/or pressure of the continuous phase which initially consists of a SCF in which the coating material is dissolved, in an autoclave in a controlled manner. This involves a reduction in one or both parameters at a specified rate to a specified value of both parameters. Adsorption of molecules of the coating material by the surface(s) to be coated is critical to the success of the process disclosed here. If this cannot be made to occur, the coating material will not be deposited upon the surface of the substrate being coated. Once adsorption of coating material on the substrate to be coated occurs, further deposition of coating material(s) will be made to occur by continued controlled reduction of T and/or P inside the autoclave until all molecules of the intended coating material originally dissolved in the SCF have been deposited on the solid surface being coated. Depending upon the amount of coating material initially dissolved in the SCF, one can produce coatings that are of molecular thickness dimensions or macroscopic thickness dimensions. The coating may be a crystalline or amorphous phase depending upon the ability of the coating material to crystallize either during or after the coating process. Further, it may be deemed desirable to adjust coating conditions such that the coating material(s) deposit on the substrate being coated in such a manner that a uniform film or coating is not produced, but a coating of some other geometry is produced. In such cases, the "coating" would form a unique geometric combination of substrate and coating material which deviates significantly in structure from a conventional film coating.

Significantly, as the temperature and pressure inside the autoclave are reduced during the coating procedure, the SCF material that forms the continuous phase in the autoclave and initially acts as a solvent for the substance being deposited as a coating generally passes from the SCF state into a binary mixture of liquid and gas phase, and as the system becomes totally depressurized, this material passes into only a gas phase. Controlled deposition of the coating material on the substrate being coated can occur at various stages of this sequence of phase changes depending upon the coating material used and its solubility in the suspending medium, originally a SCF. However, the most meaningful change in solubility properties of the coating material as temperature and pressure are altered occurs at or close to conditions that exist at the boundary between the SCF state and binary mixture of liquid and gas. Controlling the rate of change in temperature and pressure in this region is particularly important.

Because of the versatility of the coating technology disclosed herein and the ability of a SCF to produce a solution of precisely defined components, specific T and P operating conditions required to deposit a given coating material on a given substrate in a given form can vary but can be defined by the person skilled in the art for each combination of substrate being coated and coating material. When the active substance to be coated is a liquid similar considerations apply although the speed of agitation has an incidence on the size of the droplets that are coated.

In order to carry out the process of the invention, a measured weight of substrate to be coated (i.e. an emulsionable liquid or preformed particle(s) or article(s)), previously shown to be essentially insoluble in the S(,F to be used and unaffected by said SCF under conditions to be used in the coating process), is placed in an autoclave equipped with an agitator and impellor able to be turned at a defined rate. The autoclave is sealed and the agitator is started. If the substance to be coated is a solid particle, constant agitation is required but it should be relatively moderate in order to avoid any disturbance of the structural integrity of the particle. Agitation speeds can normally vary between 200 and 400 RPM. If the substance to be coated is in the form of a liquid, the control of the agitation speed is also important because it can be used to vary the size of the droplets of the emulsion formed between the supercritical fluid and the liquid active substance insoluble in it. Agitation speed for liquids normally ranges between 600 and 1000 RPM. Since the active substance to be coated is initially in a gaseous environment inside the autocalve, the agitator has no effect on the active substance at this point. However, once the system is pressurized by introducing into the autoclave from an external source a substance (e.g., $CO_2$) which is then brought to supercritical conditions by changing temperature and/or pressure inside the autoclave, the substance placed in the autoclave becomes suspended in the SCF due to the agitation provided by the agitator and impellor. Active substances suspended in the SCF due to the agitation behave much like they are suspended in a conventional liquid or liquid solution.

The next step is to introduce the desired coating material(s) into the autoclave as solute(s) dissolved in a SCF either by feeding into the autoclave a SCF solution of the desired coating material(s) or by placing the coating material inside the autoclave at the time the substrate to be coated is placed in the autoclave either as free coating material or coating material contained in a molecularly porous sac. If the coating material is placed in the autoclave in any manner, pressurization of the interior of the autoclave to produce a SCF state causes the coating material(s) present inside the autoclave to be dissolved in the SCF. In order to assure that the coating material has been solubilized, the system is equilibrated a finite time (e.g., 1 hr) before the coating process is continued.

Once a finite concentration of coating material(s) has been established in the SCF phase of the autoclave, temperature and/or pressure inside the autoclave are altered in a controlled manner so that solubility of the coating material(s) present in the initial SCF is gradually reduced, continuous agitation being maintained throughout this process. As a rule, such alteration involves reducing either the temperature or pressure in a controlled manner. Regardless of how this is accomplished, as solubility of the coating material(s) in the suspending phase of the autoclave decreases, affinity of said material(s) for the surface of the substrate being coated increases and they increasingly become adsorbed there. If solubility of the desired coating material(s) in the suspending phase is reduced at a sufficiently slow rate, the coating material(s) is transferred completely from the suspending phase onto the surface of the substrate being coated thereby forming a coating. Said coating can be deposited so that it follows the geometric shape of the substrate being coated to thereby form what is commonly termed a conformational coating. Irregularly shaped particles and articles can be so coated, so the process does not require the substrate to have a regular (e.g., spherical or sphere-like) geometry. Further, thickness of said coating can vary from molecular to macroscopic dimensions. Of course, by the time that deposition of the desired coating material(s) on the intended substrate is complete, the operating parameters of the system may be so changed that the suspending fluid is no longer a SCF, but has been transformed into a liquified state which is in equilibrium with its gaseous state. Phase diagrams that illustrate specific conditions under which these different phases exist have been established for a variety of SCF systems.

Once deposition of the desired coating material(s) is complete, the system is depressurized and the coated particle(s) or article(s) are isolated by removing them from the autoclave.

A complete schematic version of a preferred embodiment of the apparatus of the present invention is illustrated in FIG.

1. Referring now to FIG. 1, the pressured gas bottle is connected to valve 1 which delivers the gas to condenser C-1, where it is liquified. The condensed liquified gas is stored in the reservoir R-1. This liquified gas can be fed to the reservoir R-2 using valve V2. The gas phase existing in the reservoir R-1 can also be transferred to the reservoir R-2 via valve V3.

The reservoir R-2 can be used as a reaction flask and is equipped with a magnetic transmission stirrer.

The liquified gas can also be tranferred via the condenser C-2 to the pump P-1. From P-1, fluid can be fed back to reservoir via valve V4 and the condenser C-1.

Alternately, from the pump P-1, the fluid can be heated by the heat exhanger H-1 and fed to the reservoir R-2 via valve V5, or fod to the bottom side of reservoir R-3 via valve V-6, or to the top side of reservoir R-3 via valve V-7.

Liquids, solutions, fluids, subcritical fluid or supercritical fluid existing in reservoir R-2 can be taken out and transferred via valve V-8 by the pump P-2. Inversely, substances stored in pump P-2 can be introduced back inside reservoir R-2, via valve V-8. Pump P-2 can also be used to transfer materials from the reservoir R-2 via the heat exchanger H-2 to reservoir R-3 via valve V9. Possibly, valve V10 can be used to equilibrate the pressure between the pump P-2 circuit and the reservoir R-2.

Reservoir R-2 can be used as reaction flask for coating particles, for dissolving substances, for particles formations, for emulsions, for coacervation, for precipitation, for coprecipitation, for cristallisation, for desolvatation, for polymerization, for interfacial polymerisation, for polycondensation . . . . The same operation can be done in reservoir R-3, or both reservoirs can be used in the same time, or inturn of each others, or in combination to each others. Reservoir R-3 and its heating or cooling jacket is designed to create gradient of temperature and density inside, thus assuming, if necessary, an internal turbulence in the fluid during experimental conditions.

Contents of reservoir R-2 can be fed via valve V11 to the pressure controlling valve V12. In a similar way, the reservoir R-3 is also branched via V13 or V14 to the pressure controlling valve V12. Valve V12 is used to control the pressure during operations. From V12, via the heat exchanger H-3, the fluid can be decompressed in the separator S-1. From the separator S1, the gas phase can be recycled via V15 back to the reservoir R-1. All containers are equipped with a pressure jauge (PJ), an exhaut valve to atmosphere (Vair) and, or, drain valves (Vdrain).

Each reservoir and separator are equipped with separated cooling and heating jacket (TC) giving the possibility to obtain various temperatures at different places of the apparatus. The apparatus is also equipped with several windows in oder to see inside containers and with the necessary security valves and filtering devices not shown on the figure.

EXAMPLE 1

1.3 g Gelucire 50/02, an inert excipient derived from natural hydrogenated food-grade fats and oils (Source: Gattefosse S.A., F-69800 Saint Priest, France) is placed in a sealed sac formed from coffee filter paper, said sac then being attached to the shaft of the agitator placed in an autoclave (1.5 L capacity). 3.0 g HPMCP-55 (Source: Eastman, Kingsport, Tenn., USA) is then added to the autoclave as a free powder. The autoclave is sealed, agitation is initiated (430 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Gelucire 50/02 initially inside the sac sufficient time to dissolve in the SCF and migrate into the volume of the autoclave in which the particles of HPMCP-55 are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of HPMCP-55 being now suspended in the former. The autoclave is subsequently slowly depressurized to atmospheric pressure to yield particles of HPMCP-55 coated with a component of the Gelucire 50/02 (Gelucire 50/02 is a mixture of components, so the SCF process used selectively dissolves only certain components of the initial Gelucire 50/02 sample, in this case said components have a melting range of 35–40° C. as shown by differential scanning calorimetry analysis of the coated particles. When the coated HPMCP-55 particles are placed in pH 10 buffer and observed microscopically, it is found that they dissolve at a significantly slower rate than uncoated HPMCP-55 due to the presence of the coating components extracted from Gelucire 50/02 that were deposited on the various surfaces of said particles by the SCF coating process.

EXAMPLE 2

1.3 g Gelucire 50/02, an inert excipient derived from natural hydrogenated food-grade fats and oils (Source: Gattefosse S. A., F-69800 Saint Priest, France) is placed in a sealed sac formed from coffee filter paper, said sac then being attached to the shaft of the agitator placed in an autoclave (1.5 L capacity).

3.0 g bovine serum albumin (BSA) (Source: Sigrria, St. Louis, Mo., USA) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Gelucire 50/02 initially inside the sac sufficient time to dissolve in the SCF and migrate into the volume of the autoclave in which the particles of BSA are suspended in the SC $CO_2$. The temperature of the sealed autoclave is then reduced to 27° C. by cooling at an essentially linear rate over a 17 min period from 35° C. thereby causing the SC $CO_2$ suspending phase to become a mixture of liquid and gaseous $CO_2$, said particles of BSA being now suspended in the former. The autoclave is subsequently slowly depressurized to atmospheric pressure to yield particles of BSA coated with a component of the Gelucire 50/02 (Gelucire 50/02 is a mixture of components melting, so the SCF process used selectively dissolves only certain components of the initial Gelucire 50/02 sample, in this case said components have a melting range of 35–40° C. as shown by differential scanning calorimetry analysis of the coated particles. When IS the coated BSA particles are placed in water and observed microscopically, it is found that they dissolve at a slower rate than uncoated BSA due to the presence of coating material derived by extracting components from Gelucire 50/02, said components being deposited on the various surfaces of said particles by the SCF coating process disclosed.

Figure 2A:
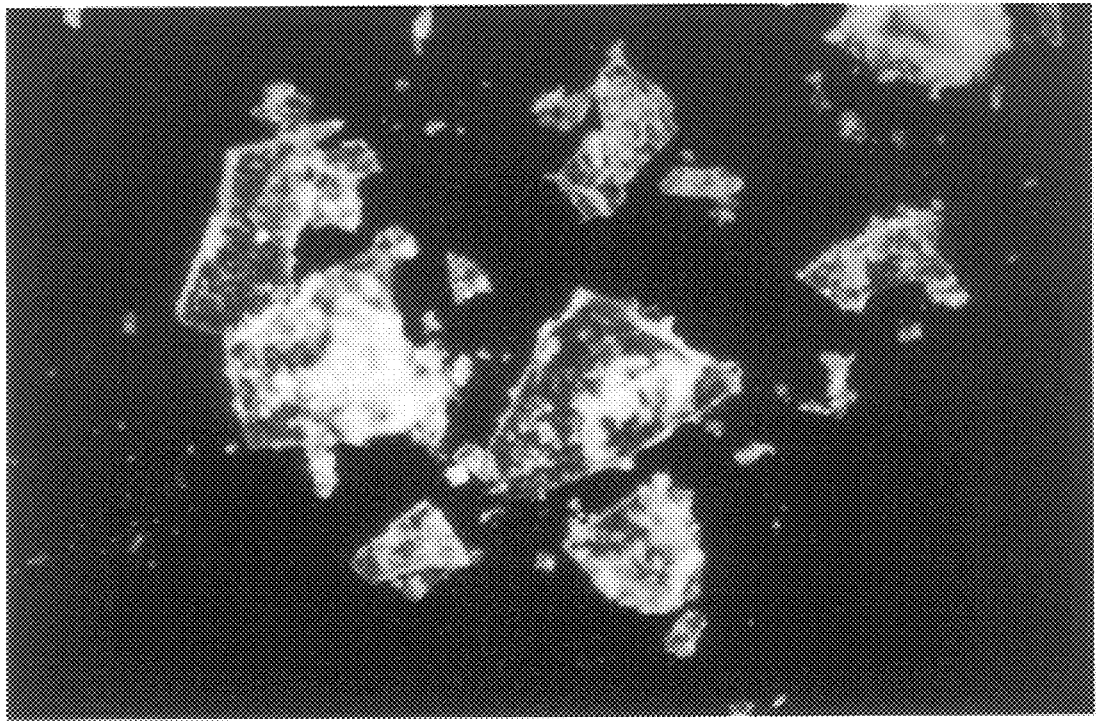
FIG. 2A is a photograph of untreated bovine serum albumine.
Figure 2B:
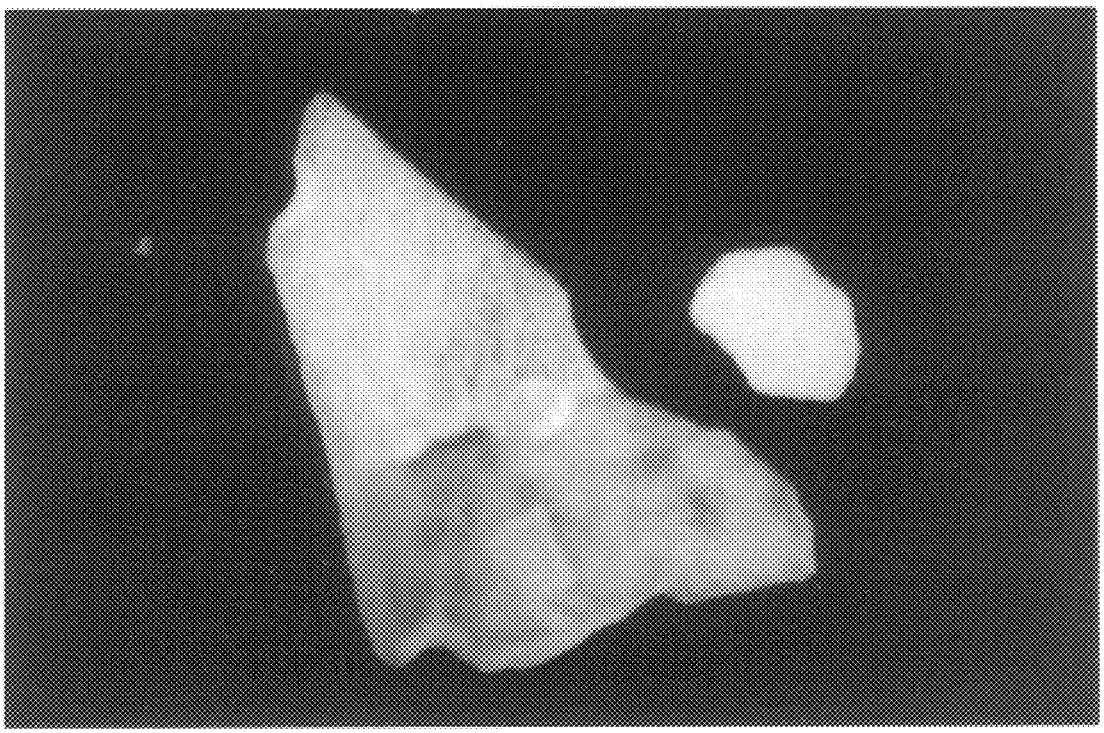
FIG. 2B is a photograph of a bovine serum albumine treated with gelucire 50/02.
Figure 3:
FIG. 3 is a photograph of juvamine treated with gelucire 50/02.
Figure 4:
FIG. 4 is a photograph of bovine serum albumine treated by Beeswax.
Figure 5:
FIG. 5 is a photograph of hemoglobin treated with Beeswax.
Figure 6:
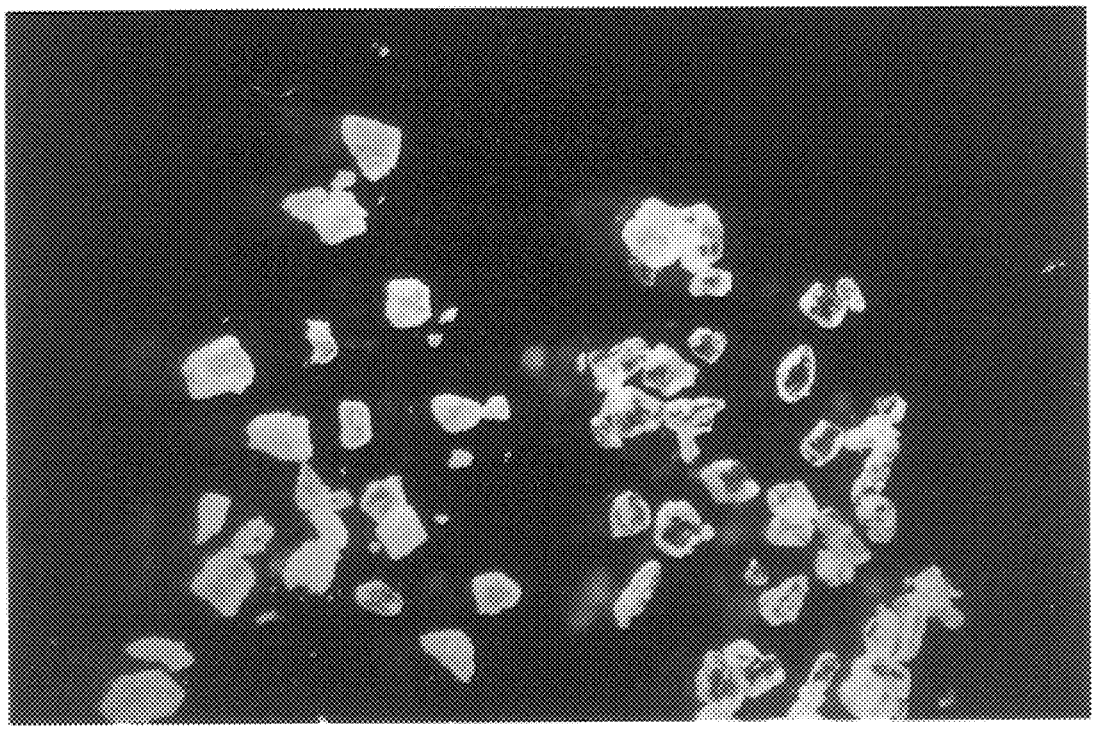
FIG. 6 shows untreated juvamine and juvamine treated by Beeswax.
Figure 7:
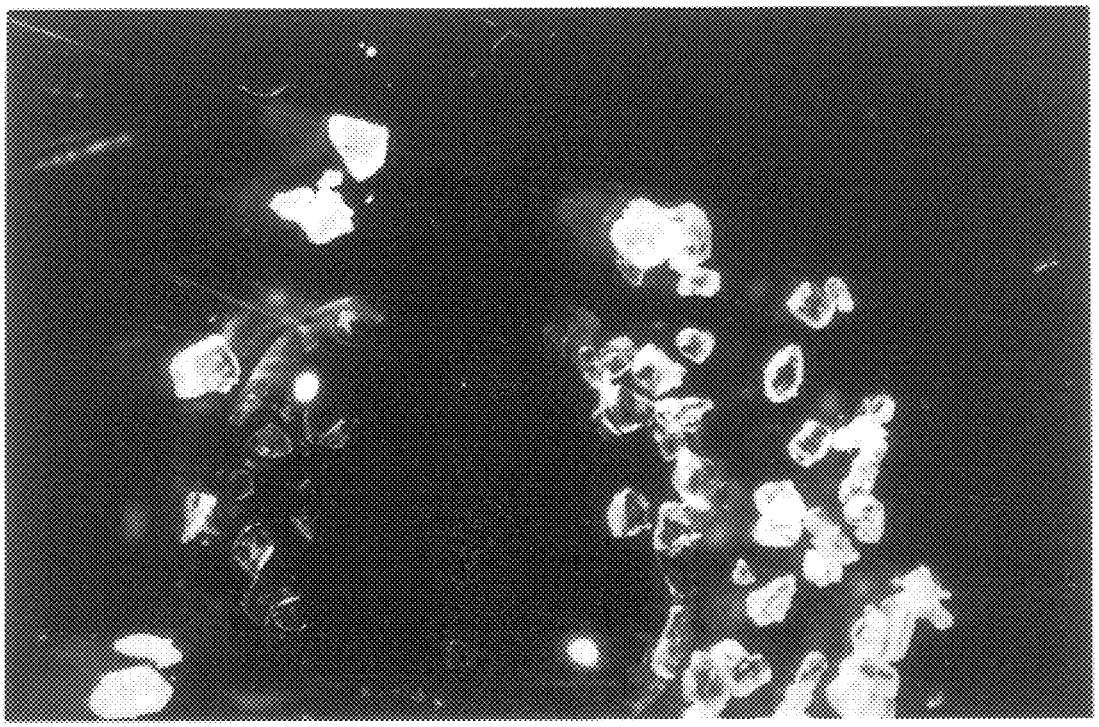
FIG. 7 is a photograph of juvamine shown in FIG. 6, 15 seconds after addition of a drop of water.
Figure 8:
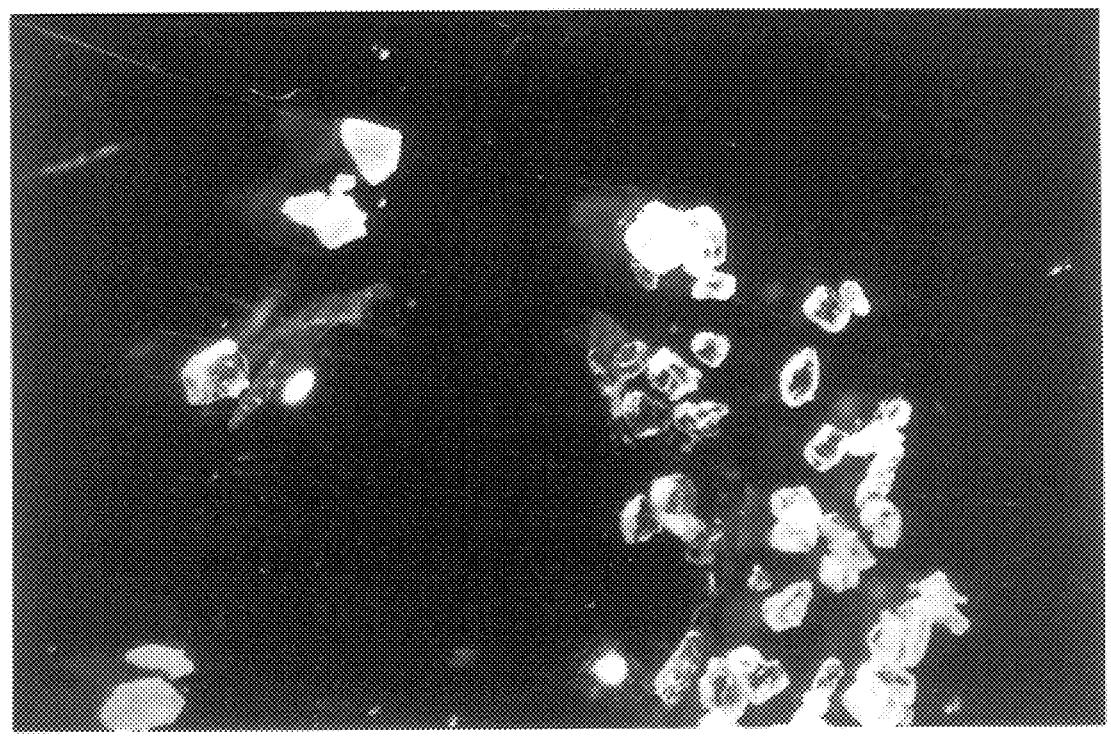
FIG. 8 is a photograph of juvamine shown in FIG. 6, 2 minutes after addition of a drop of water.

FIG. 2A shows the starting material (BSA) observed under optical microscope. It can be seen that BSA appears as thin transparent plates. FIG. 2B shows the BSA sample after treatment with Gelucire 50/02 used as the coating material. The sample is covered by a thin layer of gelucire and become opaque to the light.

EXAMPLE 3

1.3 g Gelucire 50/02, an inert excipient derived from natural hydrogenated food-grade fats and oils (Source: Gattefosse S. A., F-69800 Saint Priest, France) is placed in a sealed sac formed from coffee filter paper, said sac then being attached to the shaft of the agitator placed in an autoclave (1.5 L capacity).

3.0 g hemoglobin (Hb) (Source: Sigma, St. Louis, Mo., USA) is then added to the autoclave as a free powder. The autoclave is sealed, agitation is initiated (460 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Gelucire 50/02 initially inside the sac sufficient time to dissolve in the SCF and migrate into the volume of the autoclave in which the particles of Hb are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of Hb being now suspended in the former. The autoclave is subsequently slowly depressurized to atmospheric pressure to yield particles of Hb coated with a component of the Gelucire 50/02 (Gelucire 50/02 is a mixture of components, so the SCF process used selectively dissolves only certain components of the initial Gelucire 50/02 sample, in this case said components have a melting range of 35–40° C. as shown by differential scanning calorimetry analysis of the coated particles. When the coated Hb particles are placed in water and observed microscopically, it is found that they dissolve at a significantly slower rate than uncoated Hb due to the presence of the Gelucire 50/02 coating deposited on the various surfaces of said particles by the SCF coating process.

EXAMPLE 4

1.3 g Gelucire 50/02, an inert excipient derived from natural hydrogenated food-grade fats and oils (Source: Gattefosse S. A., F-69800 Saint Priest, France) is placed in a sealed sac formed from coffee filter paper, said sac then being attached to the shaft of the agitator placed in an autoclave (1.5 L capacity).

3.0 g erythrosine E (Source: Sigma, St. Louis, Mo., USA) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Gelucire 50/02 initially inside the sac sufficient time to dissolve in the SCF and migrate into the volume of the autoclave in which the particles of erythrosine E are suspended in the SC $CO_2$. The temperature of the sealed autoclave is then slowly reduced to 27° C. at an essentially a linear rate over a 17 min period from 35° C. thereby causing the SC $CO_2$ suspending phase to become a mixture of liquid and gaseous $CO_2$, said particles of erythrosine E being now suspended in the former. The autoclave is subsequently slowly depressurized to atmospheric pressure to yield particles of erythrosine E coated with a component of the Gelucire 50/02 (Gelucire 50/02 is a mixture of components, so the SCF process used selectively dissolves only certain components of the initial Gelucire 50/02 sample, in this case said components have a melting range of 35–40° C. as shown by differential scanning calorimetry analysis if the coated particles. When the coated erythrosine E particles are placed in water and observed microscopically, it is observed that they dissolve at a significantly slower rate than uncoated erythrosine E due to the presence of the coating deposited on the various surfaces of said particles by the SCF coating process.

EXAMPLE 5

1.3 g Gelucire 50/02, an inert excipient derived from natural hydrogenated food-grade fats and oils (Source: Gattefosse S. A., F-69800 Saint Priest, France) is placed in a sealed sac formed from coffee filter paper, said sac then being attached to the shaft of the agitator placed in an autoclave (1.5 L capacity).

3.0 g Juvamine, a commercial vitamin C formulation that contains primarily sucrose (Source: SED, Paris, France ) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Gelucire 50/02 initially inside the sac sufficient time to dissolve in the SCF and migrate into the volume of the autoclave in which the particles of Juvamine are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of Juvamine being now suspended in the former. The autoclave is subsequently slowly depressurized to atmospheric pressure to yield particles of Juvamine coated with a component of the Gelucire 50/02 (Gelucire 50/02 is a mixture of components, so the SCF process used selectively dissolves only certain components of the initial Gelucire 50/02 sample, in this case said components have a melting range of 35–40° C. as shown by differential scanning calorimetry analysis of the coated particles. When the coated Juvamine particles are placed in water and observed microscopically, it is found that they dissolve at a significantly slower rate than uncoated particles due to the presence of the coating of the Gelucire 50/02 components deposited on the various surfaces of said particles by the SCF coating process.

FIG. 3 shows a sample Juvamine covered by a thin layer of Gelucire 50/02 after 5 minutes in water. It can be seen that when the core materials is dissolved it remains a shell of gelucire which has the same shape as the covered cristal. In the central part of the picture, such shell was destroyed under the microscope by mechanical action of needle. It can be seen from the remaining material that the shell is formed by a very thin layer of gelucire.

EXAMPLE 6

5.0 g beeswax is placed in a sealed sac formed from coffee filter paper, said sac then being attached to the shaft of the agitator placed in an autoclave (1.5 L capacity). 2.0 BSA (Source: Sigma, St. Louis, Mo., USA) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Gelucire 50/02 initially inside the sac sufficient time to dissolve in the SCF and migrate into the volume of the autoclave in which the particles of BSA are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of BSA being now suspended in the former. The autoclave is subsequently slowly depressurized to atmospheric pressure to yield particles of BSA coated with a component of the beeswax (beeswax is a mixture of components, so the SCF process used selectively dissolves only certain components of the initial beeswax sample, in this case said components have a melting range of 35–45° C. as shown by differential scanning calorimetry analysis of the coated particles). When the coated BSA particles are placed on a glass slide and a drop of water is dropped on the particles on the slide, microscopic observation established that the coated BSA particles dissolved at a significantly slower rate than uncoated BSA particles due to the coating of the beeswax components deposited on the various surfaces of said particles by the SCF coating process. Indeed, it appeared that little BSA dissolved during an observation period of 5–10 min.

FIG. 4 shows BSA covered by a thin layer of beeswax. It can be seen that this sample is floating of the top a water. drop. This. shows the strong wettability difference existing between the treated sample and the starting material. Indeed the untreated starting material is completely soluble in water and thus can not stay on the surface of a water drop.

EXAMPLE 7

2.0 g paraffin wax 52–54 (Source: RP Prolabo, Paris, France) is placed in a sealed sac formed from coffee filter paper, said sac then being attached to the shaft of the agitator placed in an autoclave (1.5 L capacity). 3.0 BSA (Source: Sigma, St. Louis, Mo., USA ) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the paraffin wax 52-54 initially inside the sac sufficient time to dissolve in the SCF and migrate into the volume of the autoclave in which the particles of BSA are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of BSA being now suspended in the former. The autoclave is subsequently slowly depressurized to atmospheric pressure to yield particles of BSA coated with a component of the paraffin wax 52-54 (paraffin wax 52-54 is a mixture of components, so the SCF process used selectively dissolves only certain components of the initial paraffin wax 52-54 sample), in this case said components have a melting range of 50–52° C. as shown by differential scanning calorimetry analysis of the coated particles. When the coated BSA particles are placed on a glass slide and a drop of water is dropped on the particles on the slide, microscopic observation established that the coated BSA particles were wetted with much more difficulty than uncoated BSA particles due to the presence of the paraffin 52-54 components deposited on the various surfaces of said particles by the SCF coating process.

EXAMPLE 8

5.0 g of the triglyceride of myristic acid, sold as Dynasan 114 (Source: Huls Aktiengellschaft, D-W-4370 Marl, Germany) is placed in a sealed sac formed from coffee filter paper, said sac then being attached to the shaft of the agitator placed in an autoclave (1.5 L capacity). 1.5 g bovine serum albumin (BSA) (Source: Sigma, St. Louis, Mo., USA) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the Dynasan 114 initially inside the sac sufficient time to dissolve in the SCF and migrate into the volume of the autoclave in which the particles of BSA are suspended in the SC $CO_2$. The temperature of the sealed autoclave is then reduced to 27° C. by cooling at an essentially linear rate over a 17 min period from 35° C. thereby causing the SC $CO_2$ suspending phase to become a mixture of liquid and gaseous $CO_2$, said particles of BSA being now suspended in the former. The autoclave is subsequently slowly depressurized to atmospheric pressure to yield particles of BSA coated with a component of the Dynasan 114 sample used(it contains a mixture of components, so the SCF process used selectively dissolves only certain components of the initial Dynasan 114 sample), in this case said components have a melting range of 50–55° C. as shown by differential scanning calorimetry analysis of the coated particles.

When the coated BSA particles are placed in water and observed microscopically, it is found that they were more difficult to wet than uncoated BSA due to the presence of the Dynasan 114 components deposited on the various surfaces of said particles by the SCF coating process disclosed.

EXAMPLE 9

5.0 g of stearic acid (Source: Merck, Schuchardt, Germany) is placed in a sealed sac formed from coffee filter paper, said sac then being attached to the shaft of the agitator placed in an autoclave (1.5 L capacity). 3 g bovine serum albumin (BSA) (Source: Sigma, St. Louis, Mo., USA) is then added to the autoclave as a free powder. The autoclave is sealed, agitation is initiated (450 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the srearic acid initially inside the sac sufficient time to dissolve in the SCF and migrate into the volume of the autoclave in which the particles of BSA are suspended in the SC $CO_2$. The temperature of the sealed autoclave is then reduced to 27° C. by cooling at an essentially linear rate over a 17 min period from 35° C. thereby causing the SC $CO_2$ suspending phase to become a mixture of liquid and gaseous $CO_2$, said particles of BSA being now suspended in the former. The autoclave is subsequently slowly depressurized to atmospheric pressure to yield particles of BSA coated with a component of the stearic acid sample used (it contains a mixture of components, so the SCF process used selectively dissolves only certain components of the initial stearic acid sample), in this case said components have a melting range of 50–55° C. as shown by differential scanning calorimetry analysis of the coated particles. When the coated BSA particles are placed in water and observed microscopically, it is found that they are more difficult to wet than uncoated BSA due to the presence of the stearic acid components deposited on the various surfaces of said particles by the SCF coating process disclosed.

EXAMPLE 10

2.0 g of stearyl alcohol (Source: Janssen, Belgium) is placed in a sealed sac formed from coffee filter paper, said sac then being attached to the shaft of the agitator placed in an autoclave (1.5 L capacity). 3 g bovine serum ablbumin (BSA) (Source: Sigma, St. Louis, Mo., USA) is then added to the autoclave as a free powder. The autoclave is sealed, agitation is initiated (440 RPM), and th e interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, SO $CO_2$ inside the autoclave is in the SCF state. The system is allowed to equilibrate under these conditions for 1 hr in order to allow the Gelucire 50/13 initially inside the sac sufficient time to dissolve in the SCF and migrate into the volume of the autoclave in which the particles of BSA are suspended in the SC $CO_2$. The temperature of the sealed autoclave is then reduced to 27° C. by cooling at an essentially linear rate over a 17 min period from 35° C. thereby causing the SC $CO_2$ suspending phase to become a mixture of liquid and gaseous $CO_2$, said particles of BSA being now suspended in the former. The autoclave is subsequently slowly depressurized to atmospheric pressure to yield particles of BSA coated with a component of the stearyl alcohol sample used (it contains a mixture of components, so the SCF process used selectively dissolves only certain components of the initial stearyl alcohol sample), in this case said components have a melting range of 52–62° C. as shown by differential scanning calorimetry analysis of the coated particles. When the coated BSA particles are placed in water and observed microscopically, it is found that they are more difficult to wet than than uncoated BSA due to the presence of the stearyl alcohol components deposited on the various surfaces cf said particles by the SCF coating process disclosed.

EXAMPLE 11

2.0 g paraffin wax 52-54 (Source:RP Prolabo, Paris, France) is placed in a sealed sac formed from coffee filter paper, said sac then being attached to the shaft of the agitator placed in an autoclave (1.5 L capacity). 3.0 g hemoglobin (Hb) (Source: Sigma, St. Louis, Mo., USA) is then added to the autoclave as a free powder. The autoclave is sealed, agitation is initiated (240 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the paraffin wax 52 initially inside the sac sufficient time to dissolve in the SCF and migrate into the volume of the autoclave in which the particles of Hb are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of Hb being now suspended in the former. The autoclave is subsequently slowly depressurized to atmospheric pressure to yield particles of Hb coated with a component of the paraffin wax 52-54 (paraffin wax 52-54 is a mixture of components, so the SCF process used selectively dissolves only certain components of the initial paraffin wax 52-54 sample), in this case said components have a melting range of 50–52° C. as shown by differential scanning calorimetry analysis of the coated particles. When the coated Hb particles are placed in water and observed microscopically, it is found that they are more difficult to wet than uncoated Hb due to the presence of the paraffin wax 52-54 components deposited on the various surfaces of said particles by the SCF coating process. Numerous flat plates and needles of crystalline paraffin 52-54 were attached to the Hb particles in such a manner that they grew away from the Hb particles in essentially a perpendicular direction.

EXAMPLE 12

2.0 g paraffin wax 52 (Source: RP Prolabo, Paris, France) is placed in a sealed sac formed from coffee filter paper, said sac then being attached to the shaft of the agitator placed in an autoclave, (1.5 L capacity). 3.0 g Juvamine, a commercial mixture of vitamin C and primarily sucrose (Source: SED, Paris, France) is then added to the autoclave as a free powder. The autoclave is sealed, agitation is initiated (440 RPM), and the interior of the autoclave is pressurized by addition Of $CO_2$ to the autoclave. Once the autoclave is pressurized by the $CO_2$, the temperature of the contents of the autoclave is increased to 35° C. At this point the pressure of the interior of the autoclave is 110 bar, SO $CO_2$ inside the autoclave is in the SCF state. The system is allowed to equilibrate under these conditions for 1 hr in order to allow the paraffin wax 52 initially inside the sac sufficient time to dissolve in the SCF and migrate into the volume of the autoclave in which the particles of Juvamine are suspended in the SC $CO_2$. The temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of Juvamine being now suspended in the former. The autoclave is subsequently slowly depressurized to atmospheric pressure to yield particles of Juvamine coated with a component of the paraffin wax 52-54 (paraffin wax 52-54 is a mixture of components, so the SCF process used selectively dissolves only certain components of the initial paraffin wax 52-54 sample), in this case said components are shown to have a melting range of 50–52° C. as shown by differential scanning calorimetry analysis of the coated particles. When the coated Juvamine particles are placed in water and observed microscopically, it is found that they are more difficult to wet than uncoated Juvamine due to the presence of the paraffin wax 52-54 components deposited on the surface of said particles by the SCF coating process. When the contents of the coated particles of the Juvamine sample have completely dissolved in water, there is left a fragile shell of water-insoluble coating material that retains the geometry and external structure of uncoated crystals of sucrose, the primary component of Juvamine.

EXAMPLE 13

5.0 g beeswax (Source: APIS Centre Liegeois, VISE, Belgium) is placed in a scaled sac formed from coffee filter paper, said sac then being attached to the shaft of the agitator placed in an autoclave (1.5 L capacity). 1.9 g hemoglobin (Hb) (Source: Sigma, St. Louis, Mo., USA) is then added to the autoclave as a free powder. The autoclave is scaled, agitation is initiated (220 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the beeswax initially inside the sac sufficient time to dissolve in the SCF and migrate into the volume of the autoclave in which the particles of hemoglobin are suspended in the SC $CO_2$. The temperature of the scaled autoclave is then slowly reduced to 27° C. at an essentially linear rate over a 17 min period from 35° C. thereby causing the SC $CO_2$ suspending phase to become a mixture of liquid and gaseous $CO_2$, said particles of hemoglobin being now suspended in the former. The autoclave is subsequently slowly depressurized to atmospheric pressure to yield particles of hemoglobin coated with a component of the beeswax (beeswax is a mixture of components, so the SCF process used selectively dissolves only certain components of the initial beeswax sample). When the coated hemoglobin particles are placed in water and observed microscopically, it is found that they are more difficult to wet than uncoated hemoglobin due to the presence of the beeswax components deposited on the surface of said particles by the SCF coating process. FIG. 5 shows said coated hemoglobin particles standing on the surface of a water drop. The uncoated starting material (hemoglobin) did not behave this way because it is immediatly dissolved into the water drop.

EXAMPLE 14

5.0 g beeswax (Source: APIS Centre Liegeois, VISE, Belgium) is placed in a scaled sac formed from coffee filter paper, said sac then being attached to the shaft of the agitator placed in an autoclave (1.5 L capacity). 2.0 g Juvamine, a commercial mixture of vitamin C and primarily sucrose (Source: SED, Paris, France) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. AT this point the pressure of the interior of the autoclave is 110 bar, so $CO_2$ inside the autoclave is in the SCF state. The system is allowed to equilibrate under these conditions for 1 hr in order to allow the beeswax initially inside the sac sufficient time to dissolve in the SCF and migrate into the volume of the autoclave in which the particles of Juvamine are suspended in the SC $CO_2$. The temperature of the scaled autoclave is then slowly reduced to 25° C. at an essentially linear rate over a 20 min period from 35° C. thereby causing the SC $CO_2$ suspending phase to become a mixture of liquid and gaseous $CO_2$, said particles of Juvamine being now suspended in the former. The autoclave is subsequently slowly depressurized to atmospheric pressure to yield particles of Juvamine coated with a component of the beeswax (beeswax is a mixture of components, so the SCF process used selectively dissolves only certain components of the initial beexwas sample). When the coated Juvamine particles are placed in water and observed microscopically, it is found that they are more difficult to wet than uncoated Juvamine due to the presence of the beeswas components deposited on the surface of said particles by the SCF coating process. When the contents of the coated particles of the Juvamine sample have completely dissolved in water, there is left a fragile shell of water-insoluble coating material that retains the geometry and external structure of uncoated crystals of sucrose, the primary component of Juvamine. On FIG. 6 the left part shows untreated strating material and the beeswax coated sample is placed on the right part of the picture. This is a picture obtained under the microscope. When a drop of water is placed in such a way that it covers both samples at the same time, it can been seen (FIG. 7) that after 15 sec the cristals of the left are under dissolution while at the right the water does not dissolve the sample with the same velocity. The FIG. 8 shows the same samples after 2 minutes under the water drop, it is clear that the starting cristals are completely dissolved (on the left) and that the coated cristals (at the right) are not yet completely be dissolved.

EXAMPLE 15

5.0 g beeswax (Source: APIS Centre Liegeois, VISE, Belgium) is placed in a scaled sac formed from coffee filter paper, said sac then being attached to the shaft of the agitator placed in an autoclave (1.5 L capacity). 12 g acetaminophen is then added to the autoclave as a free powder. The autoclave is scaled, agitation is initiated (220 RPM), and the interior of the autoclave is pressurized by addition of $CO_2$, the temperature of the contents of the autoclave is increased to 35° C. At this point the pressure of the interior of the autoclave is 110 bar, so $CO_2$ inside the autoclave is in the SCF: state. The system is allowed to equilibrate uner these conditions for 1 hr in order to allow the beexwax initially inside the sac sufficient time to dissolve in the SCF and migrate into the volume of the autoclave in which the particles of acetaminophen are suspended in the SC $CO_2$. The temperature of the scaled autoclave is then slowly reduced to 27° C. at an essentially linear rate over a 17 min period from 35° C. thereby causing the SC $CO_2$ suspending phase to become a mixture of liquid and gaseous $CO_2$, said particles of acetaminophen being now suspended in the former. The autoclave is subsequently slowly depressurized to atmospheric pressure to yield particles of acetaminophen coated with a component of the beeswax (beeswax is a mixture of components, so the SCF process used selectively dissolves only certain components of the initial beeswax sample). When the coated acetaminophen particles are placed in water and observed microscopically, it is found that they are more difficult to wet than uncoated acetaminophen due to the presence of the beeswax components deposited on the surface of said particles by the SCF coating process. When the coated acetaminophen particles are tasted orally, a significant taste making effect is obtained.

EXAMPLE 16

5.0 g white beeswax (Source: Cooperation Pharmaceutique Française, Melun, France) is placed in a scaled sac formed from coffee filter paper, said sac then being attached to the shaft of the agitator placed in an autoclave (1.5 L capacity). 2.0 g Juvamine, a commercial mixture of vitamin C and primarily sucrose (Source: SED, Paris, France) is then added to the autoclave as a free powder. The autoclave is sealed, agitation is initiated (440 RPM) and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the white beeswax initially inside the sac sufficient time to dissolve in the SCF and migrate into the volume of the autoclave in which the particles of Juvamine are suspended in the SC $CO_2$. The temperature of the sealed autoclave is then slowly reduced to 25° C. at an essentially linear rate over a 20 min period from 35° C. thereby causing the SC $CO_2$ suspending phase to become a mixture of liquid and gaseous $CO_2$, said particles of Juvamine being now suspended in the former. The autoclave is subsequently slowly depressurized to atmospheric pressure to yield particles of Juvamine coated with a component of the white beeswax (white beeswax is a mixture of components, so the SCF. process used selectively dissolves only certain components of the initial white beeswax sample). When the coated Juvamine particles are placed in water and observed microscopically, it is found that they are more difficult to wet than uncoated Juvamine due to the presence of the white beeswax components deposited on the surface of said particles by the SCF coating process. When the contents of the coated particles of the Juvamine sample have completely dissolved in water, there is left a fragile shell of water-insoluble coating material that retains the geometry and external structure of uncoated crystals of sucrose, the primary component of Juvamine.

EXAMPLE 17

5.0 g white beeswax (Source: Cooperation Pharmaceutique Française, Melun, France) is placed in a sealed sac formed from coffee filter paper, said sac then being attached to the shaft of the agitator placed in an autoclave (1.5 L capacity). 2.0 g Xylitol (Source: Roquette Frères Lestrem, France) is then added to the autoclave as a free powder. the autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the white beeswax initially inside the sac sufficient time to dissolve in the SCF and migrate into the volume of the autoclave in which the particles of Xylitol are suspended in the SC $CO_2$. The temperature of the sealed autoclave is then slowly reduced to 25° C. at an essentially linear rate over a 20 min period from 35° C. thereby causing the SC $CO_2$ suspending phase to become a mixture of liquid and gaseous $CO_2$, said particles of Xylitol being now suspended in the former. The autoclave is subsequently slowly depressurized to atmospheric pressure to yield particles of Xylitol coated with a component of the white beeswax (white beeswax is a mixture of components, so the SCF process used selectively dissolves only certain components of the initial white beeswax sample). When the coated Xylitol particles are placed in water and observed microscopically, it is found that they are more difficult to wet than uncoated Xylitol due to the presence of the white beeswax components deposited on the surface of said particles by the SCF coating process.

EXAMPLE 18

5.1 g white beeswax (Source: Cooperation Pharmaceutique Française, Melun, France) is placed in a sealed sac formed from coffee filter paper, said sac then being attached to the shaft of the agitator placed in an autoclave (1.5 L capacity). 2.0 g potassium chloride (Source : Cooperation Pharmaceutique Française, Melun, France) is then added to the autoclave as a free powder. The autoclave is sealed, agitation is initiated (440 RPM), and the interior of the autoclave is pressurized by addition of $CO_2$ to the autoclave. Once the autoclave is pressurized by the $CO_2$, the temperature of the contents of the autoclave is increased to 35° C. At this point the pressure of the interior of the autoclave is 110 bar, so $CO_2$ inside the autoclave is in the SCF state. The system is allowed to equilibrate under these conditions for 1 hr in order to allow the white beeswax initially inside the sac sufficient time to dissolve in the SCF and migrate into the volume of the autoclave in which the particles of potassium chloride are suspended in the SC $CO_2$. The temperature of the sealed autoclave is then slowly reduced to 25° C. at an essentially linear rate over a 20 min period from 35° C. thereby causing the SC $CO_2$ suspending phase to become a mixture of liquid and gaseous $CO_2$, said particles of potassium chloride being now suspended in the former. The autoclave is subsequently slowly depressurized to atmospheric pressure to yield particles of potassium chloride coated with a component of the white beeswax (white beeswax is a mixture of components, so the SCF process used selectively dissolves only certain components of the initial white beeswax sample). When the coated potassium chloride particles are placed in water and observed microscopically, it is found that they are more difficult to wet than uncoated potassium chloride due to the presence of the white beeswax components deposited on the surface of said particles by the SCF coating process.

EXAMPLE 19

0.842 g Myvacet 7-07 (Source: Eastman Chemical Company, Kingsport, Tenn. 37662 U.S.A.) is place in a sealed sac formed from coffee filter paper, said sac then being attached to the shaft of the agitator placed in an autoclave (1.5 L capacity). 5 g acetaminophen is then added to the autoclave as a free powder. The autoclave is sealed, agitation is initiated (440 RPM), and the interior of the autoclave is pressurized by additon of $CO_2$ to the autoclave is increased to 35° C. At this point the pressure of the interior of the autoclave is 115 bar, so $CO_2$ inside the autoclave is in the SCF state. The system is allowed to equilibrate under these conditions for 1 hr in order to allow the beeswax initially inside the sac sufficient time to dissolve in the SCF and migrate into the volume of the autoclave in which the particles of acetaminophen are suspended in the SC $CO_2$. the temperature of the sealed autoclave is then slowly reduced to 27° C. at an essentially linear rate over a 17 min period from 35° C. thereby causing the SC $CO_2$ suspending phase to become a mixture of liquid and gaseous $CO_2$, said particles of acetaminophen being now suspended in the former. The autoclave is subsequently slowly depressurized to atmospheric pressure to yield particles of acetaminophen coated with a component of the Myvacet 7-07 (Myvacet 7-07 is a mixture of components, so the SCF process used selectively dissolves only certain components of the initial Myvacet 7-07 sample). When the coated acetaminophen particles are placed in water and observed microscopically, it is found that they are more difficult to wet than uncoated acetaminophen due to the presence of the Myvacet 7-07 components deposited on the surface of said particles by the SCF coating process.

EXAMPLE 20

4.87 g white beeswax (Source: Cooperation Pharmaceutique Française, Melun, France) is placed in a scaled sac formed from coffee filter paper, said sac then being attached to the shaft of the agitator placed in an autoclave (1.5 L capacity). 2.0 g Gentamicin sulfate (Source: Cooperation Pharmaceutique Française, Melun, France) is then added to the autoclave as a free powder. The autoclave is scaled, agitation is initiated (210 RPM), and the interior of the autoclave is pressurized by addition of $CO_2$ to the autoclave. Once the autoclave is pressurized by the $CO_2$, the temperature of the contents of the autoclave is increased to 45° C. At this point, the pressure of the interior of the autoclave is 200 bar, so $CO_2$ inside the autoclave is in the SCF state. The system is allowed to equilibrate under these conditions for 1 hr in order to allow the white beeswax initially inside the sac sufficient time to dissolve in the SCF and migrate into the volume of the autoclave in which the particles of Gentamicin sulfate are suspended in the SC $CO_2$. the temperature of the scaled autoclave is then slowly reduced to 20° C. at an essentially linear rate over a 65 min period from 45° C. thereby causing the SC $CO_2$ suspending phase to become a mixture of liquid and gaseous $CO_2$, said particles of Gentamicin sulfate being now suspended in the former. The autoclave is subsequently slowly depressurized to atmospheric pressure to yield particles of Gentamicin sulfate coated with a component of the white beeswax (white beeswax is a mixture of components, so the SCF process used selectively dissolves only certain components of the inntial white beeswas sample). When the coated Gentamicin sulfate particles are placed in water and observed microscopically, it is found that they are much more difficult to wet than uncoated Gentamicin sulfate due to the presence of the white beeswax components deposited on the surface of said particles by the SCF coating process.

EXAMPLE 21

1.0295 g Inwitor 960F (Source: Hüls France, 49100 Angers, France) is placed in a scaled sac formed from coffee filler paper, said sac then being attached to the shaft of the agitator placed in ar autoclave (1.5 L capacity). 2.0811 g D,L-Methionine (Source: Sigma, St. Louis, Mo., USA) is then added to the autoclave as a free powder. The autoclave is scaled, agitation is initiated (440 RPM), and the interior of the autoclave is pressurized by addition of CO2 to the autoclave. Once the autoclave is pressurized by the CO2, the temperature of the contents of the autoclave is increased to 45° C. At this point the pressure of the interior of the autoclave is 195 bar, so CO2 inside the autoclave is in the SCF state. The system is allowed to equilibrate under these conditions for 1 hr in order to allow the Inwitor initially inside the sac sufficient time to dissolve in the SCF and migrate into the volume of the autoclave in which the particles of D,L-Methionine are suspended in the SCCO2. The temperature of the scaled autoclave is then slowly reduced to 27° C. at an essentially linear rate over a 27 min period from 45° C. thereby causing the SC C02 suspending phase to become a mixture of liquid and gaseus CO2, said particles of D,L-Methionine being now suspended in the former. The autoclave is subsequently slowly depressurized to atmospheric pressure to yield particles of D,L-Methionine coated with a component of the Inwitor. When the coated D,L-Methionine particles are placed in water and observed microscopically, it is found that they are more difficult to wet than uncoated D,L-Methionine due to the presence of the Inwitor components deposited on the surface of said particles by the SCF coating process. Interesting taste masking is obtained.

EXAMPLE 22

0.9576 g Inwitor 960F (Source: Hüls France, 49100 Angers, France) is placed in a scaled sac formed from coffee filter paper, said sac then being attached to the shaft of the agitator placed in an autoclave (1.5 L capacity), 2.0085 g Xylitol (Source: Roquette Frères, Lestrem, France) is then added to the autoclave as a free powder. The autoclave is scaled, agitation is initiated (440 RPM), and the interior of the autoclave is pressurized by addition of CO2 to the autoclave. Once the autoclave is pressurized by the CO2, the temperature of the contents of the autoclave is increased to 45° C. At this point the pressure of the interior of the autoclave is 150 bar, so CO2 inside the autoclave is in the SCF state. The system is allowed to equilibrate under these conditions for 1 hr in order to allow the Inwitor initially inside the sac sufficient time to dissolve in the SCF and migrate into the volume of the autoclave in which the particles of Xylitol are suspended in the SCCO2. The temperature of the scaled autoclave is then slowly reduced to 27° C. at an essentially linear rate over a 27 min period from 45° C. thereby causing the SC CO2 suspending phase to become a mixture of liquid and gaseus CO2, said particles of Xylitol being now suspended in the former. The autoclave is subsequently slowly depressurized to atmospheric pressure to yield particles of Xylitol coated with a component of the Inwitor. When the coated Xylitol particles are placed in water and obseved microscopically, it is found that they are more difficult to wet than uncoated Xylitol due to the presence of the Inwitor components deposited on the surface of said particles by the SCF coating process.

EXAMPLE 23

4.9804 g Syncrowax BB4 (Source: Croda, North Humberside UK) is placed in a scaled sac formed from coffee filter paper, said sac then being attached to the shaft of the agitator placed in an autoclave (1.5 L capacity). 2,0397 g D,L-Methionine (Source: Sigma, St. Louis, Mo., USA) is then added to the autoclave as a free powder. The autoclave is sealed, agitation is initiated (440 RPM) and the interior of the autoclave is pressurized by addition of CO2 to the autoclave. Once the autoclave is pressurized by the CO2, the temperature of the contents of the autoclave is increased to 45° C. At this point the pressure of the interior of the autoclave is 190 bar, so CO2 inside the autoclave is in the SCF state. The system is allowed to equilibrate under these conditions for 1 hr in order to allow the Syncrowax initially inside the sac sufficient time to dissolve in the SCF and migrate into the volume of the autoclave in which the particles of D,L-Methionine are suspended in the SCCO2. The temperature of the scaled autoclave is then slowly reduced to 27° C. at an essentially linear rate over a 27 min period from 45° C. thereby causing the SC CO2 suspending phase to become a mixture of liquid and gaseus CO2, said particles of D,L-Methionine being now suspended in the former. The autoclave is subsequently slowly depressurized to atmospheric pressure to yield particles of D,L-Methionine coated with a component of the Syncrowax. When the coated D,L-Methionine particles are placed in water and observed microscopically, it is found that they are more difficult to wet than uncoated D,L-Methionine due to the presence of the Syncrowax components deposited on the surface of said particles by the SCF coating process. Interesting taste masking is obtained.

EXAMPLE 24

0.4567 g white beeswax (Source: Cooperation Pharmaceutique Française, Melun, France) is placed in a scaled sac formed from coffee filter paper, said sac then being attached to the shaft of the agitator placed in an autoclave (1.5 L capacity). 2,0053 g D,L-Methionine (Source: Sigma, St. Louis, Mo., USA) is then added to the autoclave as a free powder. The autoclave is scaled, agitation is initiated (440 RPM), and the interior of the autoclave is pressurized by addition of CO2 to the autoclave. Once the autoclave is pressurized by the CO2, the temperature of the contents of the autoclave is increased to 45° C. At this point the pressure of the interior of the autoclave is 185 bar, so CO2 inside the autoclave is in the SCF state. The system is allowed to equilibrate under these conditions for 1 hr in order to allow the white beeswax initially inside the sac sufficient time to dissolve in the SCF and migrate into the volume of the autoclave in which the particles of D,L-Methionine are suspended in the SCCO2. The temperature of the scaled autoclave is then slowly reduced to 27° C. at an essentially linear rate over a 27 min period from 45° C. thereby causing the SC CO2 suspending phase to become a mixture of liquid and gaseus CO2, said particles of D,L-Methionine being now suspended in the former. The autoclave is subsequently slowly depressurized to atmospheric pressure to yield particles of D,L-Methionine coated with a compoent of the white beeswax. When the coated D,L-Methionine particles are placed in water and observed microscopically, it is found that they are more difficult to wet than uncoated D,L-Methionine due to the presence of the white beeswax components deposited on the surface of said particles by the SCF coating process. Interesting taste masking is obtained.

EXAMPLE 25

0.1752 g Octadecanol (Source Janssen, Beerse Belgium) is placed in a scaled sac formed from coffee filter paper, said sac being attached to the shaft of the agitator placed in a autoclave (1.5 L capacity). 2,000 g Acetylsalicylic acid (Source: Sigma, St. Louis, Mo., USA) is then added to the autoclave as a free powder. The autoclave is scaled, agitation is initiated (440 RPM), and the interior of the autoclave is pressurized by addition of CO2 to the autoclave. Once the autoclave is pressurized by the CO2, the temperature of the contents of the autoclave is increased to 45° C. At this point the pressure of the interior of the autoclave is 160 bar, so CO2 inside the autoclave is in the SCF state. The system is allowed to equilibrate under these conditions for 1 hr in order to allow the Octadecanol initially inside the sac sufficient time to dissolve in the SCF and migrate into the volume of the autoclave in which the particles of Acetylsalicylic acid are suspended in the SCCO2. The temperature of the scaled autoclave is then slowly reduced to 27° C. at an essentially linear rate over a 27 min period from 45° C. thereby causing the SC CO2 suspending phase to become a mixture of liquid and gaseus CO2, said particles of Acetylsalicylic acid being now suspended in the former. The autoclave is subsequently slowly depressurized to atmospheric pressure to yield particles of Acetylsalicylic acid coated with a component of the Octadecanol. When the coated Acetylsalicylic acid particles are placed in water and observed microscopically, it is found that they are more difficult to wet than uncoated Acetylsalicylic acid due to the presence of the Octadecanol components deposited on the surface of said particles by the SCF coating process.

REFERENCES

1. A Review, J. W. Tom and P. G. Debenedetti, *J. Aerosol Sci.*, 22, 555–584, 1991. —Particle Formation With Supercritical Fluids—
E. M. Phillips and V. J. Stella, *Int. J. Pharm.*, 94, 1–10, 1993—Rapid Expansion From Supercritical Solutions: Application To Pharmaceutical Processes,
3. J. Bleich, B. W. Muller, and W. Wassmus, *Intl. J. Pharm.*, 97, 111–117, 1993—.Aerosol Extraction System—A New Microparticle Production Technique,
4. J. W. Tom and P. G. Debenedetti, *Biotechnol. Prog.*, 7, 403–411, 1991—.Formation of Bioerodible Polymeric Microspheres and Microparticles By Rapid Expansion of Supercritical Solutions,
5. *J. Supercrit. Fluids*, 7, 9–29, 1994.—Precipitation of Poly(L-lactic acid) and Composite Poly(L-lactic acid)—Pyrene Particles by Rapid Expansion of Supercritical Solutions,

We claim:

1. A microparticle comprising a solid particle entrapped within a coating including a layer of coating material, wherein
   the layer of said coating material is conformationally distributed on said solid particle and has a thickness ranging from the thickness of a mono-molecular layer to about 100 μm; and
   the coated microparticle has a diameter ranging from 20 nm to 100 μm when the solid particle has a spherical shape.

2. The microparticle according to claim 1, wherein the thickness of said layer of coating material ranges from the thickness of a monomolecular layer to about 40 μm.

3. The microparticle according to claim 1, wherein said solid particle is of regular but not spherical geometry or of irregular geometry, said coating material following the surface of said particle including internal pores and crevices of said solid particle.

4. The microparticle according claim 1, wherein said coating comprises a plurality of layers of identical or different coating material.

5. The microparticle according to claim 4, wherein the thickness of said layers is identical or different.

6. The microparticle according to claim 1, wherein said coating material includes fatty acids, fatty alcohols, glycerides, cholesterol, waxes, lipids and natural or synthetic polymers.

7. A composition comprising a plurality of microparticles of even or uneven size distribution comprising a solid particle conformationally entrapped within a layer of coating material having a thickness ranging from the thickness of a mono-molecular layer to about 100 μm and wherein the coated microparticle has a diameter ranging from 20 nm to 100 μm when the solid particle has a spherical shape.

8. A process for entrapping an active substance in a coating material, said process comprising the steps of:
   a. suspending said active substance which is in a solid state or absorbed in a solid substrate, in a supercritical fluid containing said coating material dissolved therein under conditions which do not cause a substantial swelling or dissolution effect on said active substance if said active substance is in the solid state; and b. gradually reducing the temperature and/or pressure of said super critical fluid under controlled condition to reduce the solubility of said coating material in said supercritical fluid to cause said coating material to be deposited onto said active substance.

9. the process according to claim 8, wherein said active substance is in the form of solid particles or dissolved in a liquid absorbed in a porous solid substrate wherein said solid particles or said porous solid substrate particles are constantly agitated during their exposure to the supercritical fluid containing the coating material dissolved therein.

10. The process according to claim 8, wherein when said active substance is a solid particle, the conditions under which said coating material is deposited on said solid particle are chosen to maintain the physical integrity of said solid particle throughout said process by avoiding solubilization of said solid particle in said supercritical fluid.

11. The process according to any one of claim 8, wherein said process comprises a further step in which said coating material deposited onto said active substance is cured in a controlled manner.

12. the process according to any one of claim 8, wherein said active substance and said coating material are placed in an autoclave which is then filled with a supercritical fluid under the conditions of temperature and pressure required to dissolve said coating material in said supercritical fluid.

13. The process according to claim 8, wherein said active substance is placed in a autoclave which is filled with a supercritical fluid containing said coating material dissolved therein.

14. An apparatus for depositing a coating material dissolved in a supercritical fluid onto an active substance, wherein said apparatus comprises:

a reservoir/reaction chamber capable of receiving and maintaining a gas under supercritical conditions, a pressurizable reaction chamber in fluid communication with said reservoir/reaction chamber, said pressurizable reaction chamber comprising stirring means to stir said active substance when said supercritical fluid containing said dissolved coating material is introduced in said reaction chamber.

15. The apparatus according to claim 14, wherein it further comprises reservoir means in fluid communication with said supercritical gas condenser for dissolving said coating material in said supercritical fluid.

16. The apparatus according to claim 14, which further comprises means for controlling temperature and pressure in said pressurizable reaction chamber.

17. The apparatus according to claim 14, wherein said stirring means comprises a magnetic transmission stirrer.

* * * * *

UNITED STATES PATENT AND TRADEMARK OFFICE

CERTIFICATE OF CORRECTION

PATENT NO.     : 6,087,003
DATED          : July 11, 2000
INVENTOR(S)    : BENOIT et al It is certified that error appears in the above-identified patent and that said letters patent is hereby corrected as shown below:

Title Page, Item [75], change "Ballwin, France" to - Ballwin, Missouri -

Signed and Sealed this

Seventeenth Day of April, 2001

*Attest:*

NICHOLAS P. GODICI

*Attesting Officer*     *Acting Director of the United States Patent and Trademark Office*